United States Patent
Onishi

(10) Patent No.: US 10,495,581 B2
(45) Date of Patent: Dec. 3, 2019

(54) DEFECT DETECTION DEVICE AND DEFECT DETECTION METHOD

(71) Applicant: SCREEN HOLDINGS CO., LTD., Kyoto (JP)

(72) Inventor: Hiroyuki Onishi, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 0 days.

(21) Appl. No.: 16/068,350

(22) PCT Filed: Dec. 14, 2016

(86) PCT No.: PCT/JP2016/087175
§ 371 (c)(1),
(2) Date: Jul. 5, 2018

(87) PCT Pub. No.: WO2017/119250
PCT Pub. Date: Jul. 13, 2017

(65) Prior Publication Data
US 2019/0011374 A1    Jan. 10, 2019

(30) Foreign Application Priority Data
Jan. 8, 2016   (JP) .................. 2016-002686

(51) Int. Cl.
*G01N 21/88* (2006.01)
*G01N 21/95* (2006.01)
*G06T 7/00* (2017.01)

(52) U.S. Cl.
CPC ..... *G01N 21/8851* (2013.01); *G01N 21/8806* (2013.01); *G01N 21/9515* (2013.01);
(Continued)

(58) Field of Classification Search
CPC ....... G01N 21/8851; G01N 2021/8825; G01N 2021/8864; G01N 21/88; G01N 21/8806; G01N 21/9515; G06T 7/00
(Continued)

(56) References Cited

U.S. PATENT DOCUMENTS 5,822,055 A    10/1998  Tsai et al.
2007/0286473 A1   12/2007  Leslie et al.
(Continued)

FOREIGN PATENT DOCUMENTS

DE     4123916 A1    1/1992
EP     0 898 163 A1  2/1999
(Continued)

OTHER PUBLICATIONS

International Search Report issued in International Application No. PCT/JP2016/087175 dated Mar. 21, 2017 (with English translation).
(Continued)

*Primary Examiner* — Tri T Ton
(74) *Attorney, Agent, or Firm* — McDermott Will & Emery LLP

(57) ABSTRACT

A plurality of images is acquired while changing the direction of light emission. Each captured image is compared with a corresponding reference image to acquire first dark regions from the captured image. Second light regions are acquired from the captured image. In a combination of one of a plurality of first dark region images indicating first dark regions and one of a plurality of second light region images indicating second light regions, a region of overlap between a first dark region and a second light region is acquired as a defect candidate region, and the existence of a defect is detected on the basis of the defect candidate region.

14 Claims, 15 Drawing Sheets

(52) U.S. Cl.
    CPC ........ *G06T 7/00* (2013.01); *G01N 2021/8825* (2013.01); *G01N 2021/8864* (2013.01)
(58) Field of Classification Search
    USPC ...................... 356/237.1–237.6, 239.1–239.8
    See application file for complete search history.

(56) References Cited

U.S. PATENT DOCUMENTS

| | | |
|---|---|---|
| 2008/0247630 A1 | 10/2008 | Horiuchi |
| 2012/0013899 A1 | 1/2012 | Amanullah |
| 2017/0122878 A1 | 5/2017 | Ono et al. |

FOREIGN PATENT DOCUMENTS

| | | |
|---|---|---|
| JP | H01-237441 A | 9/1989 |
| JP | 2002-310939 A | 10/2002 |
| JP | 2011-117788 A | 6/2011 |
| JP | 2011-149814 A | 8/2011 |
| JP | 2015-094642 A | 5/2015 |
| JP | 2015-210150 A | 11/2015 |

OTHER PUBLICATIONS

Transmittal of the International Preliminary Report on Patentability issued in corresponding International Patent Application No. PCT/JP2016/087175, dated Jul. 19, 2018, 6 pages.

Translation of the International Preliminary Report on Patentability issued in corresponding International Patent Application No. PCT/JP2016/087175, dated Jul. 19, 2018, 7 pages.

Extended European Search Report issued in corresponding European Patent Application No. 16883750.8-1230, dated Jul. 11, 2019.

1

DEFECT DETECTION DEVICE AND DEFECT DETECTION METHOD

CROSS REFERENCE

This application is the U.S. National Phase under 35 U.S.C. § 371 of International Application No. PCT/JP2016/087175, filed on Dec. 14, 2016, which claims the benefit of Japanese Application No. 2016-002686, filed on Jan. 8, 2016, the entire contents of each are hereby incorporated by reference.

TECHNICAL FIELD

The present invention relates to a technique for detecting a surface defect in an object.

BACKGROUND ART

Devices that capture images of a three-dimensional object by irradiating the object with light and inspect the external appearance of the object on the basis of the captured images are conventionally used. Techniques for changing the illumination direction during inspection are also proposed. For example, in the concrete surface inspection device disclosed in Japanese Patent Application Laid-Open No. 2011-117788, light is emitted from different directions. Grime on the concrete surface appears in every captured image, whereas defects such as cracks appear in only some of the captured images, and thus a difference image is used to detect defects.

In the flaw detector disclosed in Japanese Patent Application Laid-Open No. 2015-94642, four oblique lighting devices are turned on in order while an inspection object is illuminated from directly above by a lighting device, and an image capturing device that is located directly above captures images of the inspection object. Difference processing is carried out by performing differential computations on images of a reference inspection object prepared in advance and the acquired images, so as to detect defects in the form of dents.

Incidentally, the external appearance inspection may result in over-detection due merely to the influence of black grime. Metal components (e.g., automobile components) formed by forging or casting have undergone surface treatment such as shot blasting, and their surfaces have a three-dimensional satin-finish structure with distributed microscopic asperities. The external appearance inspection targeted for such metal components may cause over-detection due to the influence of surface asperities that are not defects.

SUMMARY OF INVENTION

The present invention is intended for a defect detection device for detecting a surface defect in an object. It is an object of the present invention to suppress over-detection of defects.

A defect detection device according to a preferable mode of the present invention includes a light emission part capable of emitting light to an object from a first direction and a second direction different from the first direction, an image capturing part for acquiring an image of a target region of a surface of the object, an image capture controller for causing the image capturing part to acquire a first captured image while the object is being irradiated with light from the first direction, and causing the image capturing part to acquire a second captured image while the object is being irradiated with light from the second direction, and a defect acquisition part for acquiring, in the first captured image, a region whose lightness is lower than a lightness of a first reference image and lower than a value that satisfies a predetermined condition as a first dark region, acquiring, in the second captured image, a region whose lightness is higher than a lightness of a second reference image and higher than a value that satisfies a predetermined condition as a second light region, acquiring a region of overlap between the first dark region and the second light region as a defect candidate region, and acquiring an existence of a defect on the basis of the defect candidate region.

According to the present invention, over-detection of defects can be suppressed.

Preferably, the light emission part is capable of emitting light to the object from three or more directions that are different from one another. Under control of the image capture controller, the image capturing part acquires three or more captured images by acquiring an image while the object is being irradiated with light from each of the three or more directions. One of the three or more captured images serves as the first captured image, and another of the three or more captured images serves as the second captured image.

More preferably, the defect acquisition part handles each of a plurality of images included in the three or more captured images as the first captured image, handles each of a plurality of images included in the three or more captured images as the second captured image, and uses a plurality of combinations of the first captured image and the second captured image to acquire the defect candidate region.

In a preferable example, the defect acquisition part acquires the defect candidate region in which the first dark region and the second light region overlap as a first defect candidate region, acquires, in the first captured image, a region whose lightness is higher than the lightness of the first reference image and higher than a value that satisfies a predetermined condition as a first light region, acquires, in the second captured image, a region whose lightness is lower than the lightness of the second reference image and lower than a value that satisfies a predetermined condition as a second dark region, acquires a region of overlap between the first light region and the second dark region as a second defect candidate region, acquires a region in which the first defect candidate region and the second defect candidate region are adjacent to each other as a third defect candidate region, and acquires an existence of a defect on the basis of the third defect candidate region.

A defect detection device according to another preferable mode of the present invention includes a light emission part capable of emitting light to an object from three or more directions that are different from one another, an image capturing part for acquiring an image of a target region of a surface of the object, an image capture controller for causing the image capturing part to acquire three or more captured images by acquiring an image while the object is being irradiated with light from each of the three or more directions, and a defect acquisition part for acquiring, in each captured image of a first predetermined number or more of captured images among the three or more captured images, a region whose lightness is lower than a lightness of a corresponding first reference image and lower than a value that satisfies a predetermined condition determined for the captured image as a first dark region, acquiring, in each captured image of a second predetermined number or more of captured images among the three or more captured images, a region whose lightness is higher than a lightness of a corresponding second reference image and higher than a value that satisfies a predetermined condition determined for the captured image as a second light region, acquiring a region of overlap between the first dark region and the second light region as a defect candidate region, and acquiring an existence of a defect on the basis of the defect candidate region.

According to the present invention, over-detection of defects can be suppressed.

In either of the above-described preferable modes, it is preferable for the defect acquisition part to expand the first dark region and the second light region and acquire a region of overlap between the first dark region and the second light region as a defect candidate region.

The present invention is also intended for a defect detection method of detecting a surface defect in an object.

A defect detection method according to a preferable mode of the present invention includes the steps of a) causing an image capturing part to acquire a first captured image of a target region of a surface of an object while the object is being irradiated with light from a first direction, b) causing the image capturing part to acquire a second captured image of the target region while the object is being irradiated with light from a second direction different from the first direction, c) acquiring, in the first captured image, a region whose lightness is lower than a lightness of a first reference image and lower than a value that satisfies a predetermined condition as a first dark region, d) acquiring, in the second captured image, a region whose lightness is higher than a lightness of a second reference image and higher than a value that satisfies a predetermined condition as a second light region, and e) acquiring a region of overlap between the first dark region and the second light region as a defect candidate region and acquiring an existence of a defect on the basis of the defect candidate region.

Preferably, the defect detection method includes the step of f) acquiring three or more captured images by causing the image capturing part to acquire an image of the target region while the object is being irradiated with light from each of three or more directions that are different from one another. The step a) and the step b) are included in the step f), and one of the three or more captured images serves as the first captured image, and another of the three or more captured images serves as the second captured image.

More preferably, the defect detection method further includes the step of g) handling each of a plurality of images included in the three or more captured images as the first captured image, handling each of a plurality of images included in the three or more captured images as the second captured image, and performing the steps c) to e) on a plurality of combinations of the first captured image and the second captured image.

A defect detection method according to another preferable mode of the present invention includes the steps of a) acquiring three or more captured images by causing an image capturing part to acquire an image of a target region of a surface of an object while the object is being irradiated with light from each of three or more directions that are different from one another, b) acquiring, in each captured image of a first predetermined number or more of captured images among the three or more captured images, a region whose lightness is lower than a lightness of a corresponding first reference image and lower than a value that satisfies a predetermined condition determined for the captured image as a first dark region, c) acquiring, in each captured image of a second predetermined number or more of captured images among the three or more captured images, a region whose lightness is higher than a lightness of a corresponding second reference image and higher than a value that satisfies a predetermined condition determined for the captured image as a second light region, and d) acquiring a region of overlap between the first dark region and the second light region as a defect candidate region and acquiring an existence of a defect on the basis of the defect candidate region.

These and other objects, features, aspects and advantages of the present invention will become more apparent from the following detailed description of the present invention when taken in conjunction with the accompanying drawings.

MODES FOR CARRYING OUT INVENTION

Figure 1:
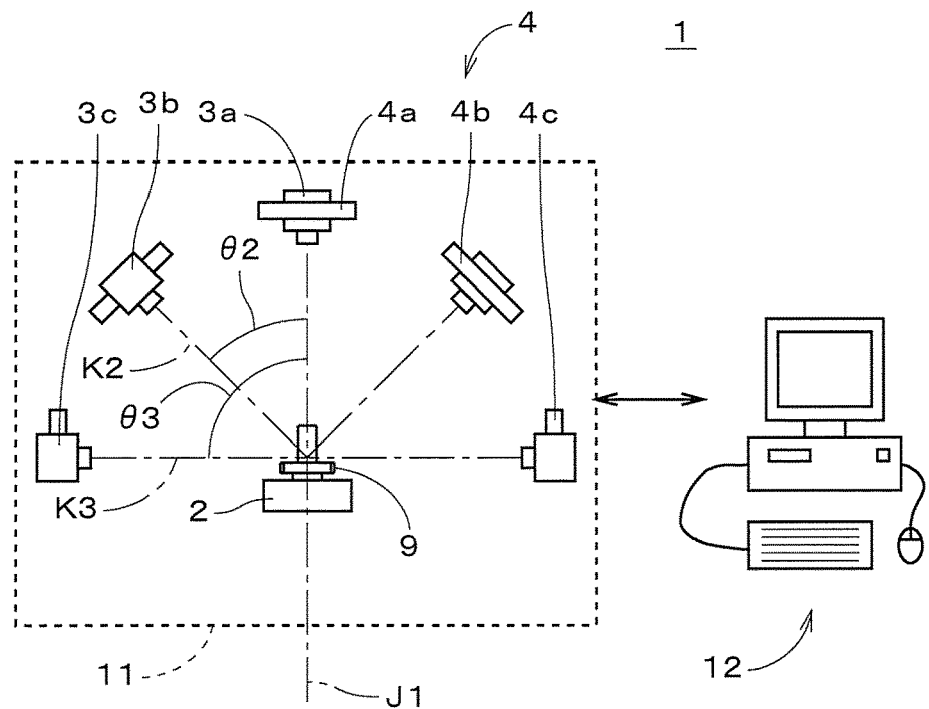
FIG. 1 illustrates a configuration of a defect detection device.
Figure 2:
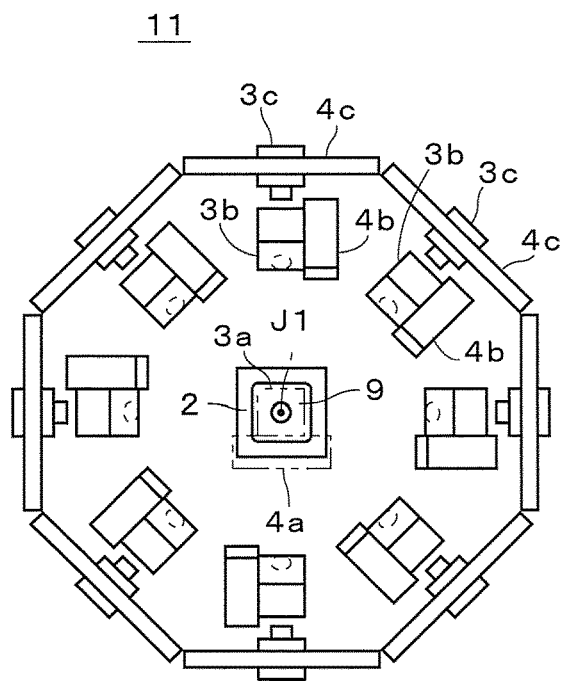
FIG. 2 is a plan view of a main body of the defect detection device.

FIG. 1 illustrates a configuration of a defect detection device 1 according to an embodiment of the present invention. FIG. 2 is a plan view of a main body 11 of the defect detection device 1. The defect detection device 1 is a device for detecting the external appearance of a three-dimensional object 9 that has a non-mirror finish surface, and detects a surface defect in the object 9. The object 9 is, for example, a metal component formed by forging or casting. The object 9 has a satin-finish surface with microscope asperities, i.e., a matte-finish surface. The surface of the object 9 has undergone shot blasting such as sandblasting. The object 9 may be any of various components (e.g., a shaft, an outer ring, or a yoke of a cylindrical hub) used for a universal joint. The surface of the object 9 may have a luster as long as the surface can scatter light to a certain degree.

Defects on the surface of the object 9 are sites where there are depressions or projections in contrast to the ideal shape thereof. Examples of the defects include dents, scratches, and machining defects. Defects may also be foreign materials adhering to the surface.

The defect detection device 1 includes the main body 11 and a computer 12 as illustrated in FIG. 1. The main body 11 includes a holder 2, a plurality of image capturing parts 3 (which are given reference signs 3a, 3b, and 3c in FIG. 1, but may collectively be indicated by reference sign 3 when there is no need to distinguish therebetween), and a light emission part 4. The object 9 is held by the holder 2. The main body 11 is provided with a light-shielding cover (not shown) that prevents external light from reaching the holder 2, and the holder 2, the image capturing parts 3, and the light emission part 4 are provided in the light-shielding cover.

In the case of automatically inspecting the entire surface of the object 9, another main body 11 may be provided, and a mechanism for turning the object 9 upside down and transporting the object 9 may be provided between the two main bodies 11.

As illustrated in FIGS. 1 and 2, the image capturing parts 3 include one upper image capturing part 3a, eight oblique image capturing parts 3b, and eight lateral image capturing parts 3c. The upper image capturing part 3a is disposed above the holder 2. The upper image capturing part 3a enables the acquisition of an image of the object 9 on the holder 2 captured from directly above.

As illustrated in FIG. 2, the eight oblique image capturing parts 3b are disposed around the holder 2 when the main body 11 is viewed vertically from above (i.e., when the main body 11 is viewed in plan view). The eight oblique image capturing parts 3b are arranged at an angular interval (angular pitch) of 45° in the circumferential direction about a central axis J1 that passes through the center of the holder 2 and points in the up-down direction. As illustrated in FIG. 1, an angle θ2 formed by an optical axis K2 of each oblique image capturing part 3 and the central axis J1 in a plane that contains the optical axis K2 and the central axis J1 is approximately 45°. Each oblique image capturing part 3b enables the acquisition of an image of the object 9 on the holder 2 captured from obliquely above. The angle θ2 is not limited to 45° as long as the image of the object 9 is captured from obliquely above, and it may preferably be set to any desired angle in the range of 15 to 75°.

Similarly to the eight oblique image capturing parts 3b, the eight lateral image capturing parts 3c are also disposed around the holder 2 when the main body 11 is viewed in plan view. The eight lateral image capturing parts 3c are arranged at an angular interval of 45° in the circumferential direction. An angle θ3 formed by an optical axis K3 of each lateral image capturing part 3c and the central axis J1 in a plane that contains the optical axis K3 and the central axis J1 is approximately 90°. Each lateral image capturing part 3c enables the acquisition of an image of the object 9 on the holder 2 captured from the side.

The upper image capturing part 3a, the oblique image capturing parts 3b, and the lateral image capturing parts 3c include CCDs (charge coupled devices) and CMOSs (complementary metal-oxide semiconductors), for example, and capture multitone images. The upper image capturing part 3a, the oblique image capturing parts 3b, and the lateral image capturing parts 3c are supported by supporters (not shown).

The light emission part 4 includes one upper light source 4a, eight oblique light sources 4b, and eight lateral light sources 4c. The upper light source 4a is adjacent to the upper image capturing part 3a. The upper light source 4a has a plurality of LEDs (light-emitting diodes) aligned perpendicular to the central axis J1, i.e., aligned horizontally. The upper light source 4a emits light to the object 9 on the holder 2 from approximately directly above.

The eight oblique light sources 4b are disposed around the holder 2 when the main body 11 is viewed in plan view. The oblique light sources 4b are respectively adjacent to the oblique image capturing parts 3b. The eight oblique light sources 4b are arranged at an angular interval of 45° in the circumferential direction. Each oblique light source 4b has a plurality of LEDs aligned approximately perpendicular to the optical axis K2. Each oblique light source 4b is capable of emitting light to the object 9 on the holder 2 from obliquely above. As illustrated in FIG. 1, an angle formed by the optical axis of each oblique light source 4b and the central axis J1 in a plane that contains the optical axis and the central axis J1 is approximately 45°. Although the optical axis K2 of each oblique image capturing part 3b and the optical axis of the adjacent oblique light source 4b do not strictly coincide, they may be regarded as coinciding in the present embodiment. Each oblique light source 4b is capable of illuminating the object 9 on the holder 2 from obliquely above. The angle formed by the optical axis and the central axis J1 is not limited to 45° as long as the object 9 is illuminated from obliquely above, and may preferably be set to any desired angle in the range of 15 to 75°.

The eight lateral light sources 4c are disposed around the holder 2 when the main body 11 is viewed in plan view. The lateral light sources 4c are respectively adjacent to the lateral image capturing parts 3c. The eight lateral light sources 4c are arranged at an angular interval of 45° in the circumferential direction. Each lateral light source 4c has a plurality of LEDs aligned approximately perpendicular to the optical axis K3 and in the horizontal direction. Thus, the eight lateral light sources 4c form a generally octagonal shape in plan view. Each lateral light source 4c is capable of emitting light to the object 9 on the holder 2 from the side. The upper light source 4a, the oblique light sources 4b, and the lateral light sources 4c may use light sources of other types different from LEDs. The light emission part 4 is capable of irradiating the object 9 with diffused light from various directions.

Figure 3:
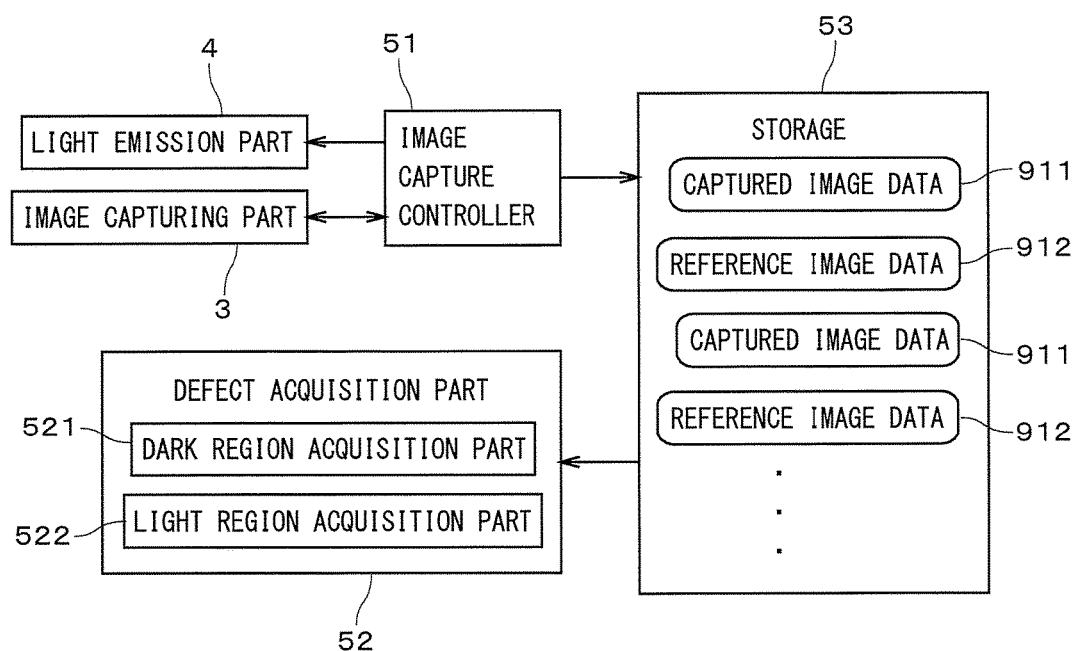
FIG. 3 is a block diagram of a functional configuration implemented by a computer.

FIG. 3 is a block diagram illustrating a functional configuration implemented by the computer 12. In FIG. 3, an image capture controller 51, a defect acquisition part 52, and a storage 53 correspond to the functions implemented by the computer 12. The image capture controller 51 controls the image capturing parts 3 and the light emission part 4. The image capture controller 51 controls these parts to acquire images of the object 9 (precisely, data indicating the images). The image data is stored in the storage 53. Although the image capturing parts 3 are illustrated as one block in FIG. 3, in actuality the upper image capturing part 3a, the oblique image capturing parts 3b, and the lateral image capturing parts 3c are connected to the image capture controller 51.

As will be described later, at least one of the 17 image capturing parts 3 acquires image data every time the image capture controller 51 controls each light source of the light emission part 4 to change the illumination state and change the direction of light emission. The image data acquired by image capture is hereinafter referred to as "captured image data." Captured image data 911 is stored in the storage 53. The storage 53 stores data of images of the ideal object 9 in each illumination state as reference image data 912. That is, ideal image data that corresponds to each illumination state of each image capturing part 3 is prepared as the reference image data 912 in the storage 53.

Figure 4:
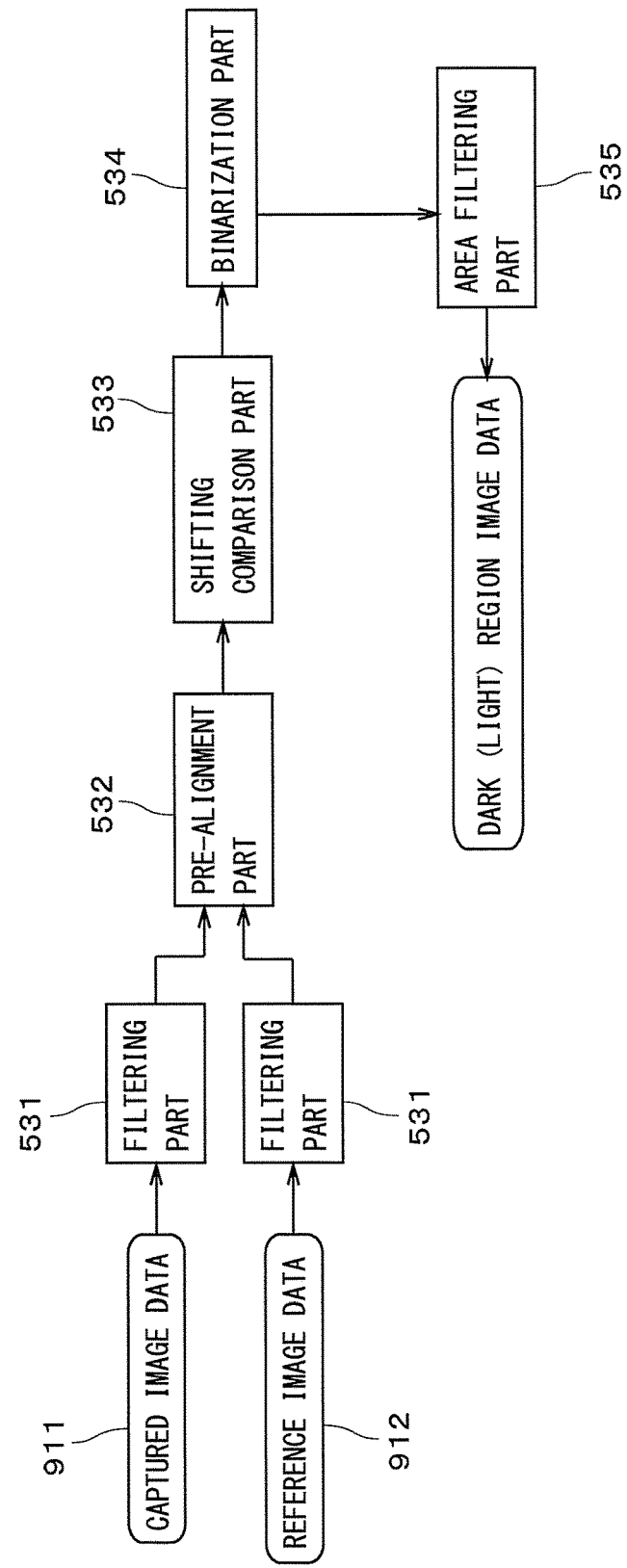
FIG. 4 illustrates a configuration of each of a dark region acquisition part and a light region acquisition part.
Figure 5:
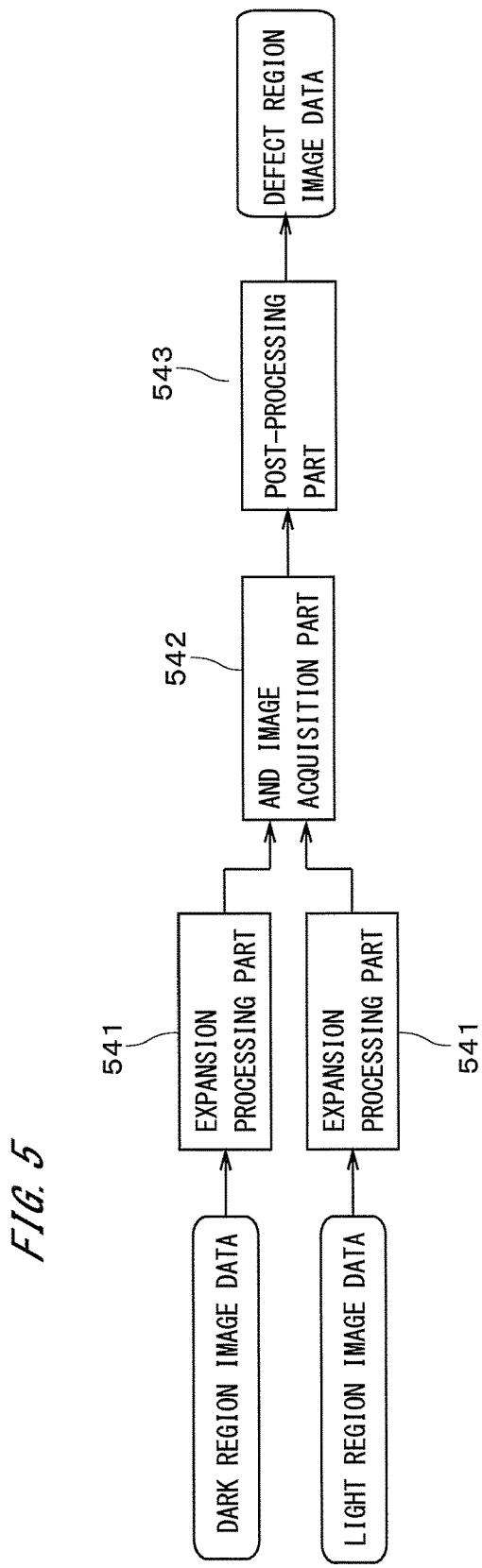
FIG. 5 illustrates a functional configuration of part of a defect acquisition part.

The defect acquisition part 52 includes a dark region acquisition part 521 and a light region acquisition part 522. FIG. 4 illustrates a configuration of each of the dark region acquisition part 521 and the light region acquisition part 522. The dark region acquisition part 521 includes two filtering parts 531, a pre-alignment part 532, a shifting comparator 533, a binarization part 534, and an area filtering part 535. The configuration of the light region acquisition part 522 is identical to that of the dark region acquisition part 521, except that different values and computations are used. FIG. 5 illustrates a functional configuration of the other part of the defect acquisition part 52. The defect acquisition part 52 further includes two expansion processing parts 541, an AND image acquisition part 542, and a post processing part 543.

Figure 6A:
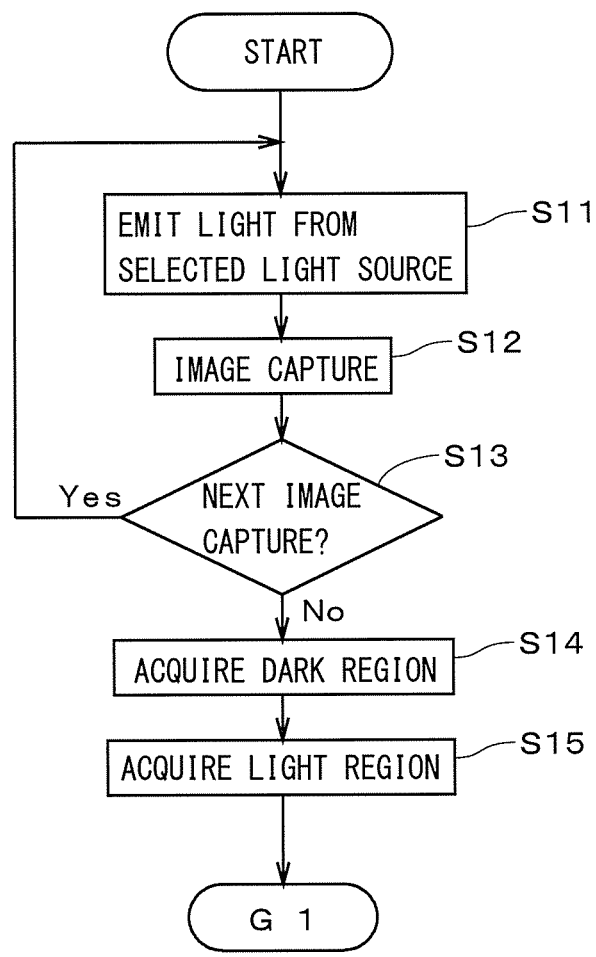
FIG. 6A illustrates the flow of operations of the defect detection device.
Figure 6B:
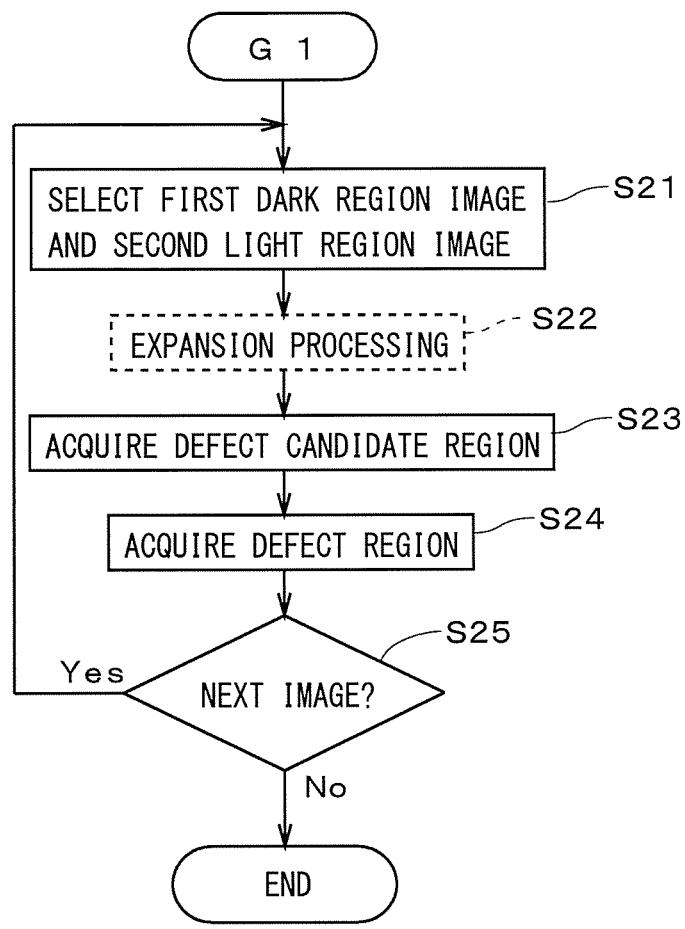
FIG. 6B illustrates the flow of operations of the defect detection device.

FIGS. 6A and 6B illustrate the flow of operations of the defect detection device 1. First, the object 9 targeted for inspection is held on the holder 2. The holder 2 is provided with an abutment part for alignment, for example, so that the object 9 is arranged in a predetermined orientation at a predetermined position when a predetermined part of the object 9 comes into contact with the abutment part. The holder 2 may also be a stage provided with positioning pins.

Next, the image capture controller 51 changes the illumination state by changing the light source that is turned on, and a selected image capturing part 3 captures an image (steps S11 and S12). Specifically, one of the lateral image capturing parts 3c is selected, then five lateral light sources 4c that are disposed continuously in the horizontal direction and centered on the selected lateral image capturing part 3c are selected and turned on one by one in order, and the lateral image capturing part 3c captures an image every time each lateral light source 4c is turned on. These operations are repeated while changing the lateral image capturing part 3c. In actuality, multiple lateral image capturing parts 3c capture images in each illumination state in order to shorten the operating time. Moreover, all of the lateral light sources 4c are turned on and all of the lateral image capturing parts 3c capture images. Accordingly, each lateral image capturing part 3c acquires six images.

In the case of the oblique image capturing parts 3b, one of the oblique image capturing parts 3b is selected, then one of the eight oblique light sources 4b is selected one by one in order and turned on, and the oblique image capturing part 3b captures an image every time each selected oblique light source 4b is turned on. These operations are repeated while changing the oblique image capturing part 3b. In actuality, all of the oblique image capturing parts 3b capture images in each illumination state in order to shorten the operating time. Moreover, all of the oblique light sources 4b are turned on and all of the oblique image capturing parts 3b capture images. All of the oblique image capturing parts 3b also capture images when only the upper light source 4a is turned on. Accordingly, each oblique image capturing part 3b acquires 10 images.

In the case of the upper image capturing part 3a, 10 images are acquired while changing the illumination state as in the case of the oblique image capturing parts 3b. In the actual operation, the upper image capturing part 3a captures an image when the oblique image capturing parts 3b capture an image, which shortens the operating time. As described above, the selected image capturing part 3 repeatedly captures an image while the image capture controller 51 changes the illumination state by changing the light source that is turned on (step S13).

The captured image data is stored as the captured image data 911 in the storage 53. The acquired images are hereinafter referred to as "captured images." In the storage 53, data of reference images that correspond to each captured image is prepared as the reference image data 912. The reference images indicate the object 9 that has no defects in the same illumination states as those of the captured images. The reference image data 912 may be acquired by capturing images of the object 9 that has no defects, or may be acquired as data indicating an average image of a large number of images of the object 9.

In order to simplify the description, processing that is performed on image data may hereinafter simply be described as processing that is performed on images. Description is given on only processing that focuses on one of the image capturing parts 3. The same processing is also performed on the other image capturing parts 3.

First, one of the captured images is selected as a first captured image. A reference image corresponding to the first captured image is selected as a first reference image. As illustrated in FIG. 4, captured image data 911 of the first captured image and reference image data 912 of the first reference image are input to the filtering parts 531.

The two filtering parts 531 each perform a filtering process of reducing noise such as median filtering or Gaussian filtering on the first captured image and the first reference image. After the filtering process, the first captured image and the first reference image are output to the pre-alignment part 532. The pre-alignment part 532 specifies the amounts of positional and angular displacements of the first reference image relative to the first captured image through pattern matching using a predetermined pattern. Then, the first reference image is moved in parallel and rotated relative to the first captured image by the amounts of positional and angular displacements between the two images, so that the position and angle of the first reference image are approximately aligned with those of the first captured image. In this way, the two images are pre-aligned.

The shifting comparator 533 obtains evaluation values that indicate a difference between the first captured image and the first reference image while moving the first reference image little by little in the top, bottom, right, and left directions from the pre-aligned position. For example, the obtained evaluation values is a sum of the absolute values for (signed) differences of pixel values in a region of overlap between the two images. The shifting comparator 533 then acquires an image that indicates signed differences in pixel value between the two images at a position at which the evaluation value is a minimum.

The binarization part 534 binarizes the signed difference image with a predetermined value to acquire a first dark region image. In actuality, the signed difference image is not obtained, in order to simplify the processing. Specifically, the values of pixels in the difference image are obtained by subtracting the value of each pixel in the first captured image from the value of the corresponding pixel in the first reference image and if the obtained value is negative, setting the value to zero. A positive value is prepared in advance, and in the difference image, regions each composed of pixels having values greater than or equal to the positive value are acquired as first dark regions. In general terms, in the first captured image, regions whose lightness is lower than the lightness of the first reference image and whose absolute values of the differences in lightness are greater than or equal to a first reference value are acquired as the first dark regions. The first reference value is a positive value. In yet other words, in the first captured image, regions whose lightness is lower by a predetermined value or more than the lightness of the first reference image are acquired as the first dark regions. In the case of a monochrome image, pixel values may be regarded as lightness, and in the case of a color image, values obtained by performing a predetermined computation on the values of pixels of each color component are treated as lightness.

The first dark regions may be derived from the ratio between the value of each pixel in the first reference image and the value of the corresponding pixel in the first captured image. Specifically, the value of each pixel in the first reference image is divided by the value of the corresponding pixel in the first captured image so as to obtain the values of pixels in a ratio image. The first reference value greater than one is prepared in advance, and in the ratio image, regions each composed of pixels having values greater than or equal to the first reference value are acquired as the first dark regions. The values of pixels in the ratio image may, of course, be obtained by diving the value of each pixel in the first captured image by the value of the corresponding pixel in the first reference image. In this case, in the ratio image, regions each composed of pixels having values less than or equal to a first reference value smaller than one are acquired as the first dark regions.

The first reference value does not necessarily have to be a constant. The first reference value may be a function of the lightness or pixel values of the first reference image and/or the first captured image. The first reference value may be determined using the difference and ratio between the lightness or pixel values of the first reference image and the lightness or pixel values of the first captured image, or may be determined using other computations. The fact that the first reference value may be determined in various ways applies also to second to fourth reference values, which will be described later. The first to fourth reference values do not necessarily have to be the same value, and may be calculated in different ways. In general terms, in the first captured image, regions whose lightness is lower than the lightness of the first reference image and lower than the value that satisfies a predetermined condition are acquired as the first dark regions. The "predetermined condition" may be set individually for each captured image. Also, a plurality of "predetermined conditions" may be used for one captured image. For example, the first reference value may be set such that dark regions are unlikely to be detected at positions at which pixel values tend to change for every image capture, such as edges in the captured image. The above description applies also to light regions and the other dark regions, which will be described later.

When the first dark regions have been acquired, the area filtering part 535 deletes first dark regions whose areas are smaller than a predetermined value and acquires an image that indicates the remaining first dark regions as a first dark region image. The multiple captured images acquired by the image capturing parts 3 are sequentially selected as the first captured image, so that the same number of first dark region images as the number of captured images is acquired (step S14).

Next, one of the captured images is selected as a second captured image. A reference image corresponding to the second captured image is selected as a second reference image. In the light region acquisition part 522, captured image data 911 of the second captured image and reference image data 912 of the second reference image are respectively input to the filtering parts 531 and subjected to a filtering process in the same manner as in the dark region acquisition part 521. The pre-alignment part 532 performs pre-alignment of the second captured image and the second reference image. The shifting comparator 533 obtains evaluation values and acquires an image that indicates signed differences in pixel value between the two images. The signed difference image is binarized with a predetermined value to acquire a second light region image.

In actuality, the signed difference image is not obtained, in order to simplify the processing as in the case of acquiring the first dark regions. Specifically, the values of pixels in the difference image are obtained by subtracting the value of each pixel in the second reference image from the value of the corresponding pixel in the second captured image and if the obtained value is negative, setting the value to zero. A positive value is prepared in advance, and in the difference image, regions each composed of pixels having values greater than or equal to the positive value are acquired as second light regions. In general terms, in the second captured image, regions whose lightness is higher than the lightness of the second reference image and whose absolute values of the differences in lightness are greater than or equal to a second reference value are acquired as the second light regions. The second reference value is a positive value. In yet other words, in the second captured image, regions whose lightness is higher by a predetermined value or more than the lightness of the second reference image are acquired as the second light regions.

The second light regions may be acquired using various techniques, as in the case of the first dark regions. In the case where the second light regions are derived from the ratio between the value of each pixel in the second captured image and the value of the corresponding pixel in the second reference image, for example the value of each pixel in the second captured image is divided by the value of the corresponding pixel in the second reference image so as to obtain the values of pixels in a ratio image. A second reference value greater than one is prepared in advance, and in the ratio image, regions each composed of pixels having values greater than or equal to the second reference value are acquired as the second light regions. The values of pixels in the ratio image may, of course, be obtained by dividing the value of each pixel in the second reference image by the value of the corresponding pixel in the second captured image. In this case, in the ratio image, regions each composed of pixels having values less than or equal to a second reference value smaller than one are acquired as the second light regions. In general terms regarding the case of the first dark regions, in the second captured image, regions whose lightness is higher than the lightness of the second reference image and higher than the value that satisfies a predetermined condition are acquired as the second light regions.

Thereafter, the area filtering part 535 deletes second light regions whose areas are smaller than a predetermined value and acquires an image that indicates the remaining second light regions as a second light region image. The multiple captured images acquired by the image capturing parts 3 are sequentially selected as the second captured image, so that the same number of second light region images as the number of captured images is acquired (step S15).

Figure 7A:
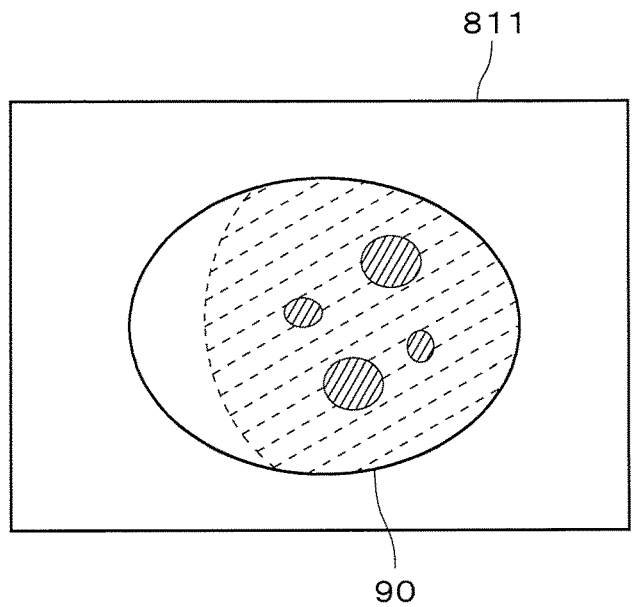
FIG. 7A illustrates a first captured image.
Figure 7B:
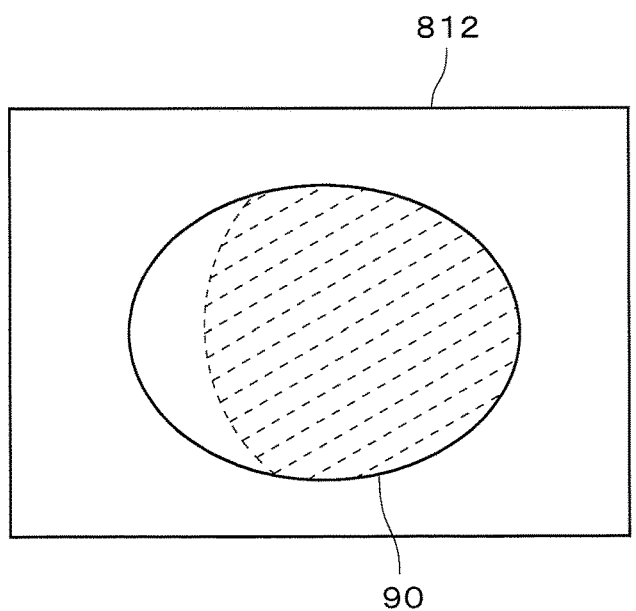
FIG. 7B illustrates a first reference image.
Figure 7C:
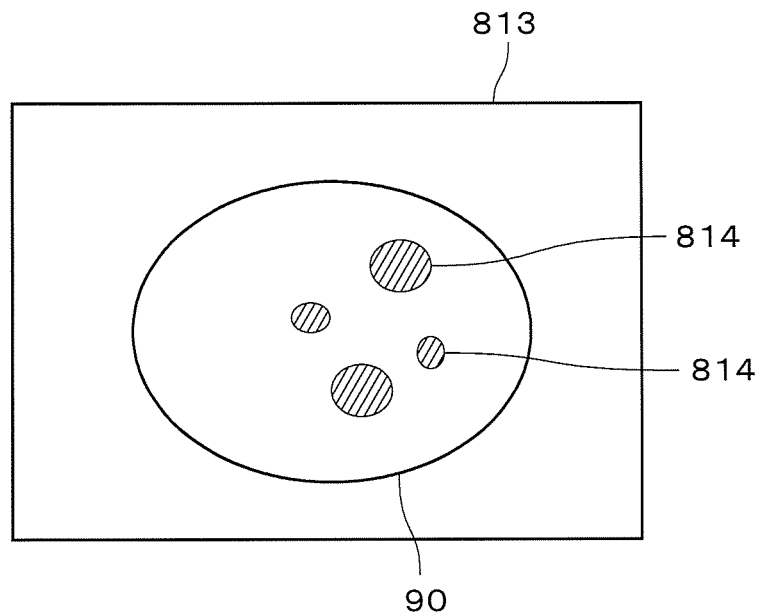
FIG. 7C illustrates a first dark region image.

FIGS. 7A to 7C and FIGS. 8A to 8C illustrate examples of the above-described processing. A region of the surface of the object 9 that appears in the captured image is hereinafter referred to as a "target region 90." The image capturing parts 3 and the target regions 90 are in one-to-one correspondence, and each image capturing part 3 always acquires an image of the same target region 90. In FIGS. 7A to 7C and 8A to 8C, the target region 90 is illustrated in an abstract oval shape. FIG. 7A illustrates an example of a first captured image 811. FIG. 7B illustrates an example of a first reference image 812. A difference image between the two images (or a ratio image therebetween; the same applies below) is binarized to acquire a first dark region image 813 illustrated in FIG. 7C. In the target region 90 of the first dark region image 813, regions where the first captured image 811 is darker than the first reference image 812 and that satisfy a predetermined condition are acquired as first dark regions 814. In the present embodiment, the values of pixels in the first dark regions 814 are "1," and the values of pixels in the other region are "0."

Figure 8A:
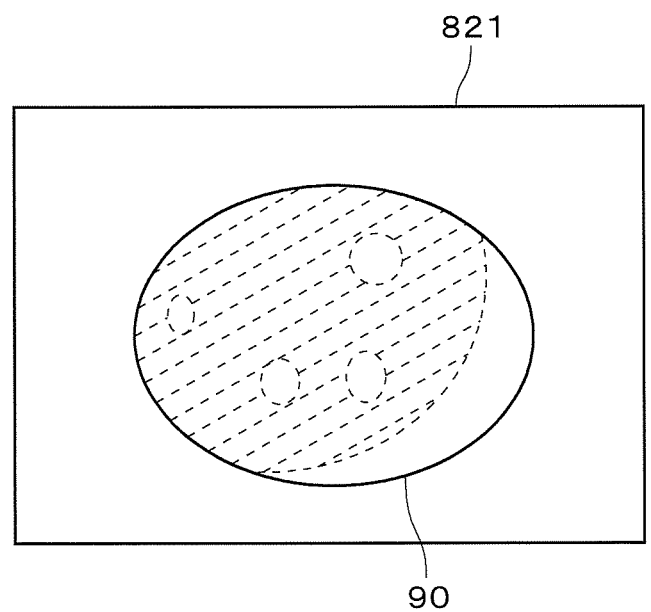
FIG. 8A illustrates a second captured image.
Figure 8B:
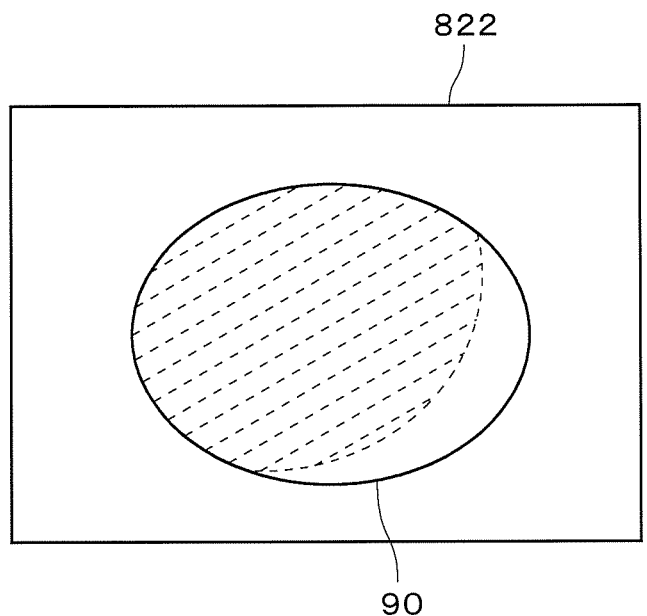
FIG. 8B illustrates a second reference image.
Figure 8C:
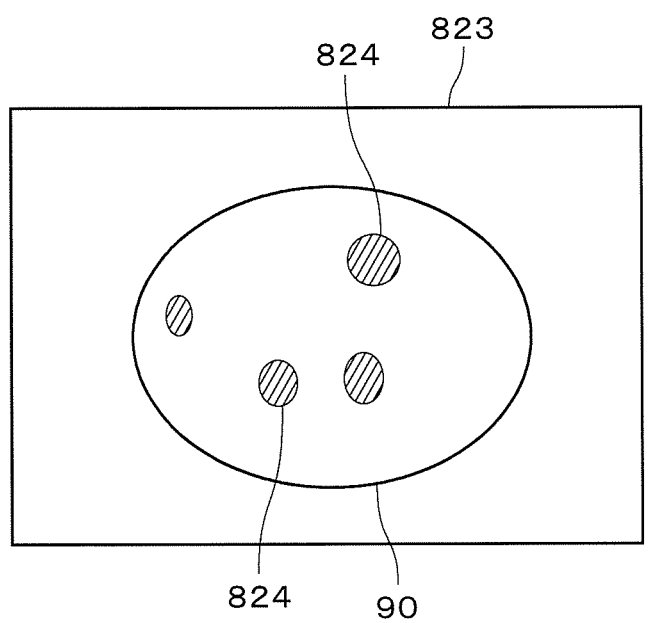
FIG. 8C illustrates a second light region image.

FIG. 8A illustrates an example of a second captured image 821. FIG. 8B illustrates an example of a second reference image 822. A difference image between the two images is binarized to acquire a second light region image 823 illustrated in FIG. 8C. In the target region 90 of the second light region image 823, regions where the second captured image 821 is lighter than the second reference image 822 and that satisfy a predetermined condition are acquired as second light regions 824. In the present embodiment, the values of pixels in the second light region 824 are "1," and the values of pixels in the other region are "0."

Next, one of the first dark region images and one of the second light region images are selected (step S21), and data of these images is input to the expansion processing parts 541 as illustrated in FIG. 5. In FIG. 5, these pieces of image data are respectively referred to as "dark region image data" and "light region image data." In this way, expansion processing is performed on the first dark regions and the second light regions (step S22). The amount of expansion is determined in advance. Note that the expansion processing may be omitted.

Figure 9:
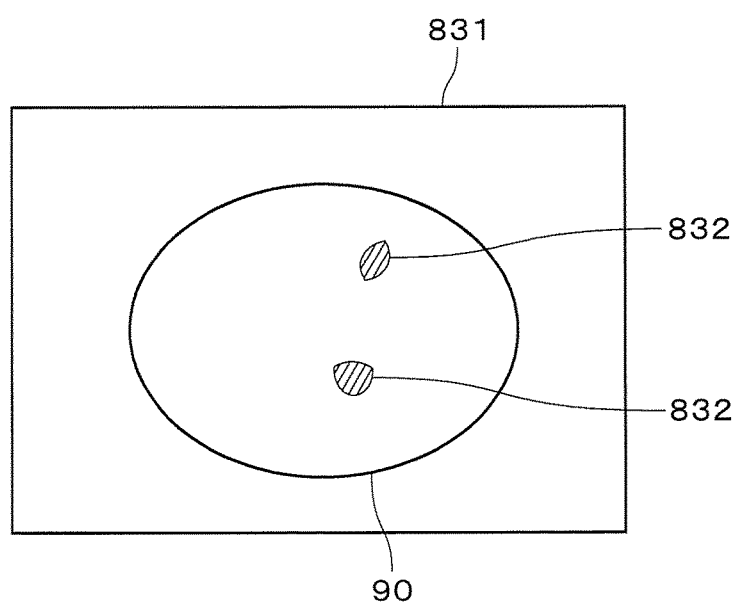
FIG. 9 illustrates a defect candidate region image.

The AND image acquisition part 542 obtains an AND image of the first dark region image and the second light region image. That is, at each corresponding position in the first dark region image and the second light region image, only the pixel having a pixel value of "1" in both of the two images is acquired as an image having a value of "1." In this way, regions of overlap between the first dark regions and the second light regions are acquired as defect candidate regions. For example, a defect candidate region image 831 that indicates defect candidate regions 832 in FIG. 9 is acquired from the first dark region image 813 in FIG. 7C and the second light region image 823 in FIG. 8C (step S23).

The post processing part 543 deletes unnecessary defect candidate regions and outputs defect region image data that is data of an image indicating defect regions (step S24). The post processing may involve various types of processing such as deleting minute regions, and the existence of defects is acquired on the basis of the defect candidate regions. Defect region as used herein is a region that implies the existence of a defect, and is not a region that indicates the contour of a defect. The existence of defects is acquired through the acquisition of defect regions.

When the processing for acquiring defect regions has been completed for one pair of the first dark region image and the second light region image, this combination of the regions is changed and steps S21 to S24 are repeated (step S25). Specifically, steps S21 to S24 are performed for one first dark region image while changing the second light region image in order, and thereafter, the first dark region image is changed and steps S21 to S24 are performed therefor while changing the second light region image in order. Through the above-described processing, in the case where there is a defect, the position of the defect is detected in the target region 90 viewed from one image capturing part 3.

Note that the same image may be selected as the first captured image and the second captured image if the expansion processing is performed. This enables detection of minute defects such as fine scratches. That is, the first dark region image and the second light region image may be derived from the same captured image.

The computer 12 displays one of the captured images on its display such that defect regions, first dark regions that are irrelevant to the defect regions, i.e., do not overlap with the defect regions, and second light regions that do not overlap with the defect regions are displayed in different colors on the target region 90. This enables an operator to easily be aware of how defects have been detected.

In the case where the surface of the object 9 has defects such as projecting or depressed defects or defects caused by adhesion of foreign materials, those defects may appear light or dark in captured images if directional light is applied to the surface. If defects are to be detected using only either dark regions or light regions, false defects will be detected due to microscopic surface asperities, which results in over-detection of defects. In view of this, the defect detection device 1 uses the first dark region image and the second light region image in order to suppress over-detection of defects.

For example, in the case where a defect appears in the form of a pair of dark and light regions when light is applied from a certain direction, a defect can be detected by detecting a pair of dark and light regions in one image. However, achieving high defect detection accuracy is not easy because it is unknown how far away from each other such a pair will appear and both light and dark regions do not always appear. Also, defects have complex shapes, and it is not easy in many cases to determine the direction of light emission in which defects appear dark or light. In view of this, the defect detection device 1 detects defects for all combinations of the first dark region image and the second light region image, thereby achieving defect detection with high accuracy.

There are, of course, cases where the illumination state (i.e., illumination direction) for the case where first dark regions appear in captured images due to the existence of defects and the illumination state for the case where second light regions appear in captured images due to the existence of defects are known. In this case, defects may be detected at high speed by determining, in advance, a first direction that is the direction of light emission when first dark regions appear and a second direction that is the direction of light emission when second light regions appear. In the above-described case, the light emission part 4 need only emit light to the object 9 from the first direction and the second direction different from the first direction, and the image capture controller 51 causes an image capturing part 3 to acquire the first captured image while the object 9 is being irradiated with light from the first direction, and causes the same image capturing part 3 to acquire the second captured image while the object 9 is being irradiated with light from the second direction.

The "first direction" and the "second direction" refer roughly to the directions of light emission, and it is not intended to limit light to parallel light in the case where light is emitted from only the first and second directions. The light emitted from the first direction may be light that is emitted from directions deviating from the first direction. In other words, light is emitted from at least one light source whose position is skewed toward the first direction.

A minimum number of captured images is two, and preferably, three or more captured images may be acquired. That is, the light emission part 4 is capable of emitting light to the object 9 from three or more directions that are different from one another, and under the control of the image capture controller 51, each image capturing part 3 acquires an image while the object 9 is being irradiated with light from each of the three or more directions. In the case where preferable directions of light emission are known, one of the three or more captured images acquired on the basis of that information is selected as the first captured image and another of the three or more captured images is selected as the second captured image. By preparing three or more captured images, more appropriate defect detection can easily be achieved.

Although in the above-described embodiment, the defect acquisition part 52 handles each of three or more captured images as a first captured image and each of the three or more captured images as a second captured image and acquires defect candidate regions using all combinations of the first captured image and the second captured image, all of the captured images do not necessarily have to be used. Also, the processing for acquiring defect candidate regions does not necessarily have to be performed for all combinations of the first captured image and the second captured image, i.e., all combinations of the first dark region image and the second light region image.

In other words, the defect acquisition part 52 handles each of a plurality of images included in the three or more captured images as a first captured image and each of a plurality of images (which do not necessarily have to be the same as the above-described plurality of images used in the case of the first captured image) included in the three or more captured images as a second captured image, and acquires defect candidate regions using a plurality of combinations of the first captured images and the second captured images.

Figure 10:
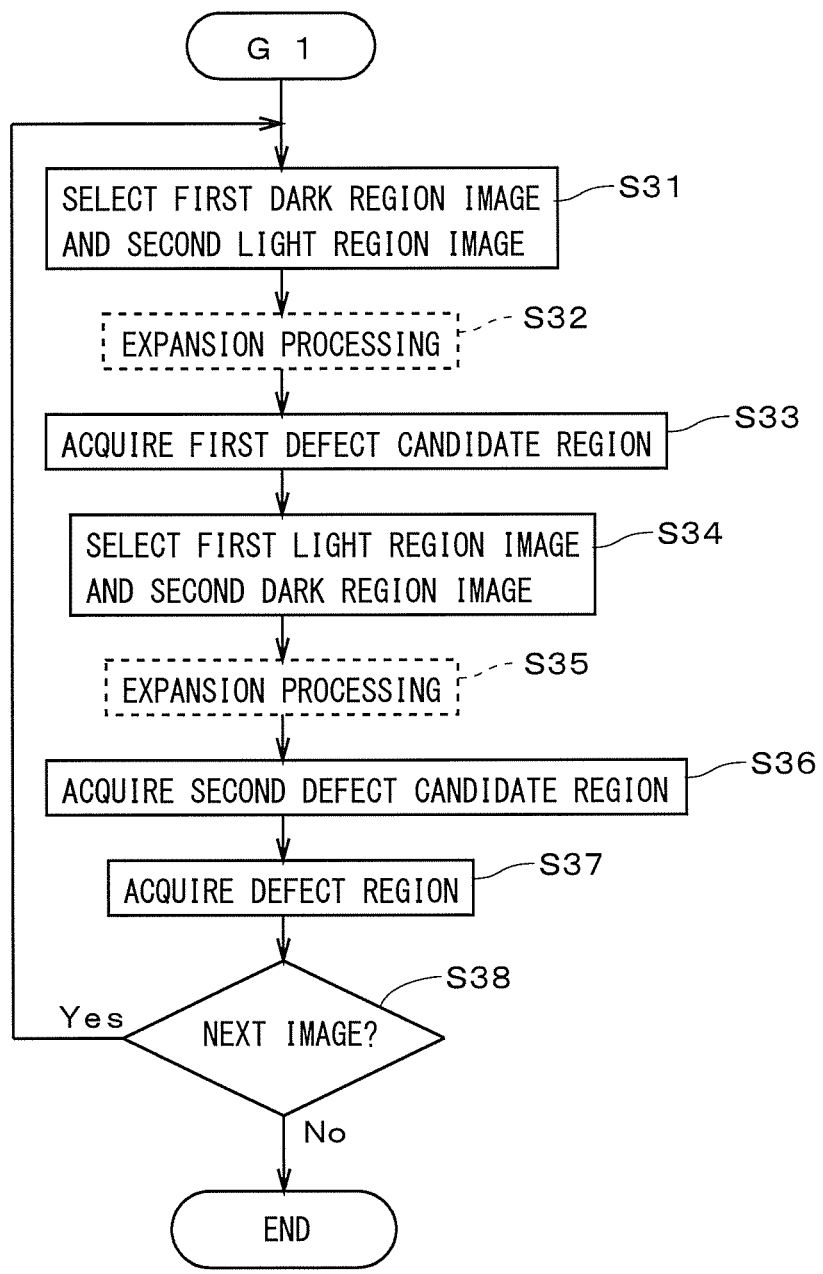
FIG. 10 illustrates another example of operations for defect detection.

FIG. 10 is a diagram for describing another example of the defect detection operation performed by the defect detection device 1. FIG. 10 corresponds to FIG. 6B, and steps S31 to S33 are identical to steps S21 to S23 in FIG. 6B. In steps S31 to S33, defect candidate regions are acquired as first defect candidate regions. Next, a light region image and a dark region image that are obtained by interchanging the first and second captured images that are used to acquire the first defect candidate regions are respectively selected as a first light region image and a second dark region image (step S34).

That is, the first light region image is an image obtained in the following manner as in step S15 in FIG. 6A. First, the values of pixels in a difference image are obtained by subtracting the value of each pixel in the first reference image from the value of the corresponding pixel in the first captured image and if the obtained value is negative, setting the value to zero. A positive value is prepared in advance, and in the difference image, regions each composed of pixels having values greater than or equal to the positive value are acquired as first light regions. In general terms, in the first captured image, regions whose lightness is higher than the lightness of the first reference image and whose absolute values of the differences in lightness are greater than or equal to a third reference value are acquired as the first light regions. The third reference value is a positive value. In yet other words, in the first captured image, regions whose lightness is higher by a predetermined value or more than the lightness of the first reference image are acquired as the first light regions. As described previously, a ratio image may be used instead of the difference image, and more complex conditions may be used. In general terms, in the first captured image, regions whose lightness is higher than the lightness of the first reference image and higher than the value that satisfies a predetermined condition are acquired as the first light regions. Thereafter, the area filtering part 535 deletes first light regions whose areas are smaller than a predetermined value and acquires an image that indicates the remaining first light regions as the first light region image.

The second dark region image is an image obtained in the following manner as in step S14 in FIG. 6A. First, the values of pixels in a difference image are obtained by subtracting the value of each pixel in the second captured image from the value of the corresponding pixel in the second reference image and if the obtained value is negative, setting the value to zero. A positive value is prepared in advance, and in the difference image, regions each composed of pixels having values greater than or equal to the positive value are acquired as second dark regions. In general terms, in the second captured image, regions whose lightness is lower than the lightness of the second reference image and whose absolute values of the differences in lightness are greater than or equal to a fourth reference value are acquired as the second dark regions. The fourth reference value is a positive value. In yet other words, in the second captured image, regions whose lightness is lower by a predetermined value or more than the lightness of the second reference image are acquired as the second dark regions. As described previously, a ratio image may be used instead of the difference image, and more complex conditions may be used. In general terms, in the second captured image, regions whose lightness is lower than the lightness of the second reference image and lower than the value that satisfies a predetermined condition are acquired as the second dark regions. Thereafter, the area filtering part 535 deletes second dark regions whose areas are smaller than a predetermined value and acquires an image that indicates the remaining second dark regions as the second dark region image.

The first light regions and the second dark regions are subjected to expansion processing, and an AND image that indicates regions of overlap between the two regions is acquired as a second defect candidate region image that indicates second defect candidate regions (steps S35 and S36).

Figure 11:
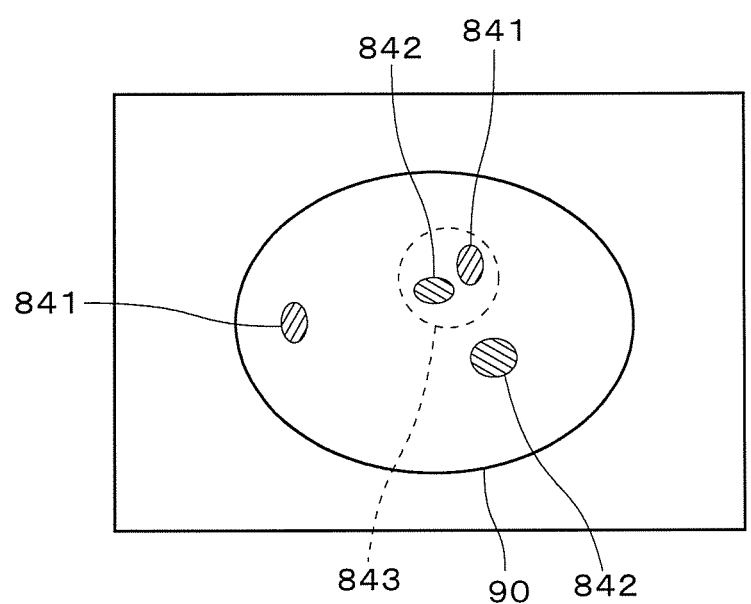
FIG. 11 illustrates how a third defect candidate region is selected.

The post processing part 543 deletes those of the first and second defect candidate regions whose areas are smaller than or equal to a predetermined value. Then, those of the first defect candidate regions and the second defect candidate regions that are adjacent to one another are acquired as third defect candidate regions. FIG. 11 illustrates how a third defect candidate region is selected. Reference sign 841 indicates first defect candidate regions, and reference sign 842 indicates second defect candidate regions. Among these regions, a pair indicated by reference sign 843 is selected as a third defect candidate region.

Whether a first defect candidate region and a second defect candidate region are adjacent to each other may be determined in various ways. For example, if the distance between the centroid of a first defect candidate region and the centroid of a second defect candidate region is less than or equal to a predetermined value, the first defect candidate region and the second defect candidate region may be determined to be adjacent to each other. Alternatively, if the shortest distance between a first defect candidate region and a second defect candidate region is less than or equal to a predetermined value, the first defect candidate region and the second defect candidate region may be determined to be adjacent to each other.

The third defect candidate regions may be output directly as defect regions, or part of the third defect candidate regions may be output as defect regions (step S37). For example, it is possible to omit the step of deleting those of the first and second defect candidate regions whose areas are smaller than or equal to a predetermined value and to delete those of the third defect candidate regions whose first and second defect candidate regions both have an area smaller than or equal to a predetermined value. The existence of defects is acquired on the basis of the third defect candidate regions.

Next, the processing for acquiring third defect candidate regions is performed for another combination of the first dark region image and the second light region image and for the first light region image and the second dark region image that correspond to that combination (steps S31 to S37). By repeating steps S31 to S37, the processing for acquiring third defect candidate regions is performed for all combinations of the first dark region images and the second light region images and for the first light region images and the second dark region images that correspond to those combinations (step S38). Accordingly, defects of various shapes are detected in the target region 90. The acquisition of the third defect candidate regions further suppresses over-detection in the case where over-detection of false defects occurs frequently with only the first defect candidate regions.

The processing for acquiring third defect candidate regions may additionally involve a step of determining whether each defect has a depressed shape or a projecting shape. The direction of light emission can be determined from the position of the light source that is on. Meanwhile, the direction from the centroid of a first dark region to the centroid of a second light region can be acquired when a first defect candidate region included in a third defect candidate region is acquired. If this direction is approximately in the illumination direction, a defect can be said to have a depressed shape. Instead of the centroid, other center positions such as the center of a circumscribed circle or the center of a minimum circumscribed rectangle may be used. Similarly, in the case where the direction from the centroid of a second dark region to the centroid of a first light region is approximately in the illumination direction when a second defect candidate region included in a third defect candidate region is acquired, a defect can be said to have a depressed shape. In the case where the defect has a projecting shape, the positional relationship of the dark region and the light region is reversed.

Whether a defect has a depressed shape or a projecting shape can in principle be determined from the positional relationship of the first dark region and the second light region forming a pair. This information is, however, not highly reliable, and therefore the positional relationship of the second dark region and the first light region forming another pair is also used to improve the reliability of determining the shape of the defect. For example, in the case where the direction from the centroid of the first dark region to the centroid of the second light region is not in the direction of light emission but cannot be said to be in the opposite direction, a defect may be determined to have a depressed shape if the direction from the centroid of the second dark region to the centroid of the first light region is approximately in the illumination direction.

Figure 12:
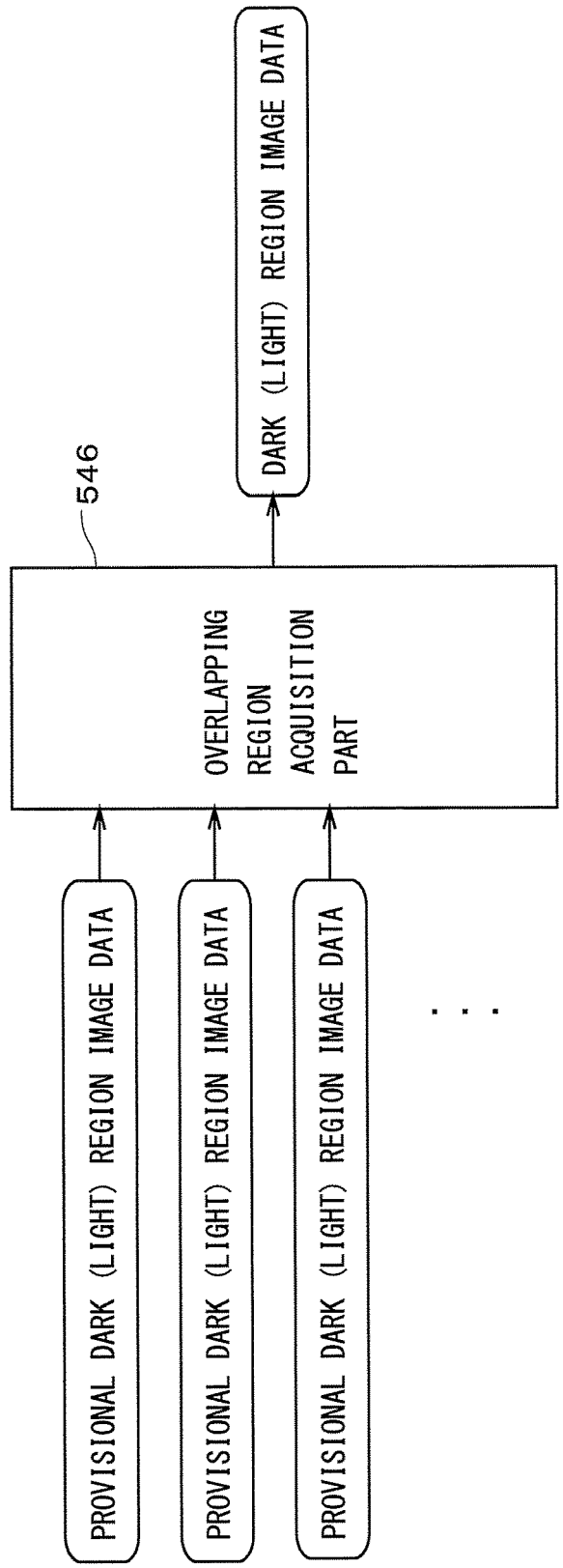
FIG. 12 illustrates a configuration that is added to the defect acquisition part in yet another example of operations.

FIG. 12 illustrates a configuration that is added to the defect acquisition part 52 according to yet another example of operations of the defect detection device 1. An overlapping region acquisition part 546 in FIG. 12 is provided between each of the dark region acquisition part 521 and the light region acquisition part 522 in FIG. 4 and the configuration illustrated in FIG. 5. The aforementioned image data generated by the dark region acquisition part 521 is hereinafter referred to as "provisional first dark region image data," and the aforementioned image data generated by the light region acquisition part 522 is hereinafter referred to as "provisional second light region image data." The image indicated by the provisional first dark region image data is referred to as a "provisional first dark region image," and first dark regions included in the provisional first dark region image are referred to as "provisional first dark regions." The image indicated by the provisional second light region image data is referred to as a "provisional second light region image," and second light regions included in the provisional second light region image are referred to as "provisional second light regions."

One of the overlapping region acquisition parts 546 receives input of a plurality of pieces of provisional first dark region image data and outputs first dark region image data. The other overlapping region acquisition part 546 receives input of a plurality of pieces of provisional second light region image data and outputs second light region image data.

Figure 13:
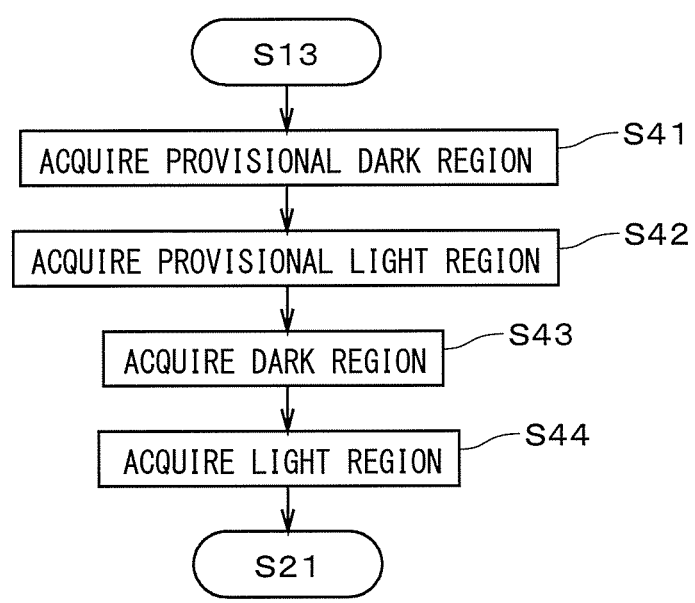
FIG. 13 illustrates part of the flow of operations of the defect detection device.

FIG. 13 illustrates part of the flow of operations of the defect detection device 1. The operations in FIG. 13 are performed between step S13 in FIG. 6A and step S21 in FIG. 6B. First, data of the same number of provisional first dark region images as the number of captured images, i.e., a plurality of pieces of provisional first dark region image data indicating provisional first dark regions, is generated through the same processing as that in step S14 in FIG. 6A (step S41). Also, data of the same number of provisional second light region images as the number of captured images, i.e., a plurality of pieces of provisional second light region image data indicating provisional second light regions, is generated through the same processing as that in step S15 (step S42). The "predetermined condition" for acquiring first dark regions, as referred to in the description of step S14, may differ for each of the plurality of provisional first dark region images that is acquired. Similarly, the "predetermined condition" for acquiring second light regions, as referred to in the description of step S15, may differ for each of the plurality of provisional second light region images that is acquired.

All pieces of provisional first dark region image data are input to the overlapping region acquisition part 546. The overlapping region acquisition part 546 acquires regions of overlap among a predetermined number or more of provisional first dark regions among all the provisional first dark regions, as first dark regions (step S43). Specifically, the overlapping region acquisition part 546 acquires overlapping regions by summing the values of corresponding pixels in all the provisional first dark region images and binarizing the summed image with a predetermined threshold value. In general terms regarding the above-described processing, in each captured image of a first predetermined number or more of captured images among the three or more captured images, regions whose lightness is lower than the lightness of the corresponding first reference image and lower than the value that satisfies a predetermined condition determined for the captured image are acquired as first dark regions.

Figure 14:
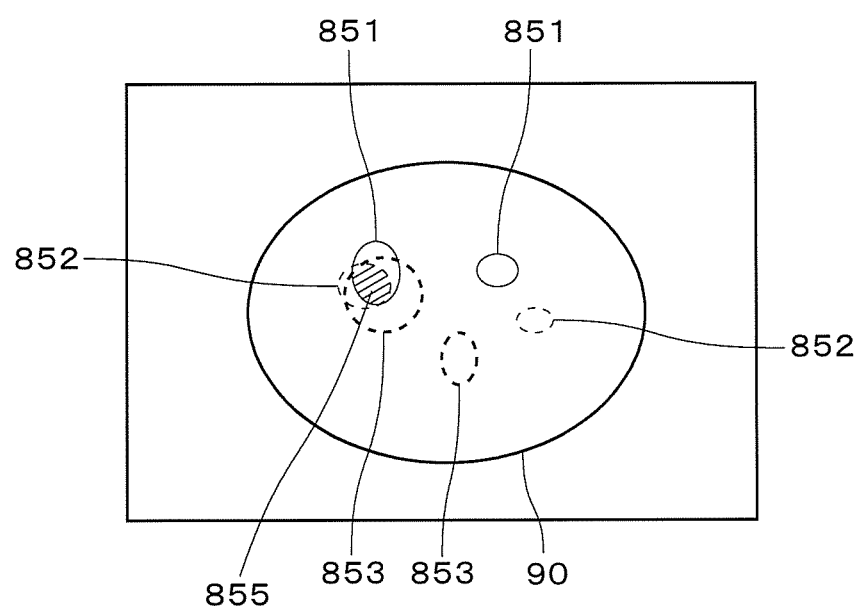
FIG. 14 is a diagram for describing processing performed by an overlapping region acquisition part.

FIG. 14 is a diagram for describing the processing performed by the overlapping region acquisition part 546. Reference sign 851 indicates provisional first dark regions in one provisional first dark region image. Reference sign 852 indicates provisional first dark regions in another provisional first dark region image. Reference numeral 853 indicates provisional first dark regions in yet another provisional first dark region image. In the case where regions of overlap among three or more provisional first dark regions are acquired as first dark regions, a region indicated by reference sign 855 is acquired as a first dark region. Note that the aforementioned "first predetermined number" may be "1." In this case, in any of the three or more captured images, regions whose lightness is lower than the lightness of the corresponding first reference image and lower than the value that satisfies a predetermined condition determined for the captured image are acquired as first dark regions.

All pieces of provisional second light region image data are also input to the overlapping region acquisition part 546 and subjected to the same processing as in the case of the provisional first dark region image data. That is, the overlapping region acquisition part 546 acquires regions of overlap among a predetermined number or more of provisional second light regions among all the provisional second light regions, as second light regions (step S44). In general terms regarding the above-described processing, in each captured image of a second predetermined number or more of captured images among the three or more captured images, regions whose lightness is higher than the lightness of the corresponding second reference image and higher than the value that satisfies a predetermined condition determined for the captured image are acquired as second light regions. Note that the aforementioned "second predetermined number" may be "1." In this case, in any of the three or more captured images, regions whose lightness is higher than the lightness of the corresponding second reference image and higher than the value that satisfies a predetermined condition determined for the captured image are acquired as second light regions.

The configuration illustrated in FIG. 5 performs steps S22 to S24 illustrated in FIG. 6B on the image data indicating the first dark regions and the image data indicating the second light regions, both having been generated through the above-described processing. Accordingly, regions of overlap between the first dark regions and the second light regions are acquired as defect candidate regions. Then, defect regions that indicate the existence of defects are acquired on the basis of the defect candidate regions. Note that the above-described operations do not include steps S21 and S25, which are repeat steps, because one first dark region image and one second light region image are acquired. However, for example, a plurality of first dark region images and a plurality of second light region images may be generated by performing step S43 on a plurality of combinations of provisional first dark region images differently selected from among a plurality of provisional first dark region images and performing step S44 on a plurality of combinations of provisional second light region images differently selected from among a plurality of provisional second light region images. In this case, steps S21 and S25 are performed.

The above-described example of operations suppresses over-detection of first dark regions and second light regions, thus suppressing over-detection of defects.

The defect detection device 1 described above may be modified in various ways.

The arrangement and numbers of the light sources 4a, 4b, and 4c and the image capturing parts 3 may be appropriately changed. The illumination state of the light emission part 4 may be modified in various ways. The plurality of light sources may be turned on two at a time or three at a time. The light emission part 4 may change the direction of light emission by moving the light sources.

The computer 12 may be implemented by dedicated hardware, or part of the computer 12 may be implemented by dedicated hardware. In the case of high-speed external appearance inspection, it is preferable for parallel processing to be performed by a computer or dedicated hardware.

The processing order may be appropriately changed as long as substantially the same processing is performed. The processing order illustrated in the above-described embodiment is merely one example. For example, the second captured image may be selected every time the first captured image is selected, and a defect candidate region image may be acquired every time these images are selected. The defect candidate regions may be treated directly as defect regions.

The reference images may be generated from captured images. That is, dark regions and light regions may be acquired by a so-called self-comparison method. For example, a reference image in which dark defects disappear is acquired by performing processing for expanding light regions and then performing reduction processing on a captured image. A reference image in which light defects disappear may be acquired by performing processing for reducing light regions and then performing expansion processing on a captured image.

The defect detection device 1 may be used to detect defects on the surfaces of other objects such as various types of substrates having patterns or films. The defect detection device 1 is in particular suitable for the inspection of objects that are likely to cause over-detection due to their surfaces including satin-finish regions (which are not limited to metallic surfaces).

The configurations of the above-described preferred embodiments and variations may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

REFERENCE SIGNS LIST

1 Defect detection device
3a, 3b, 3c Image capturing part
4 Light emission part
9 Target object
51 Image capture controller
90 Target region
541 Expansion processing part
811 First captured image
812 First reference image
814 First dark region
821 Second captured image
822 Second reference image
824 Second light region
832 Defect candidate region
841 First defect candidate region
842 Second defect candidate region
843 Third defect candidate region
851 to 853 Provisional first dark region
855 First dark region
S11 to S15, S21 to S25, S41 to S44 Step

The invention claimed is:
1. A defect detection device for detecting a surface defect in an object, comprising:
a light emission part capable of emitting light to an object from a first direction and a second direction different from said first direction;
an image capturing part for acquiring an image of a target region of a surface of said object;

an image capture controller for causing said image capturing part to acquire a first captured image while said object is being irradiated with light from said first direction, and causing said image capturing part to acquire a second captured image while said object is being irradiated with light from said second direction; and a defect acquisition part for acquiring, in said first captured image, a region whose lightness is lower than a lightness of a first reference image and lower than a value that satisfies a predetermined condition as a first dark region, acquiring, in said second captured image, a region whose lightness is higher than a lightness of a second reference image and higher than a value that satisfies a predetermined condition as a second light region, acquiring a region of overlap between said first dark region and said second light region as a defect candidate region, and acquiring an existence of a defect on the basis of said defect candidate region.

2. The defect detection device according to claim 1, wherein said light emission part is capable of emitting light to said object from three or more directions that are different from one another, under control of said image capture controller, said image capturing part acquires three or more captured images by acquiring an image while said object is being irradiated with light from each of said three or more directions, and one of said three or more captured images serves as said first captured image, and another of said three or more captured images serves as said second captured image.

3. The defect detection device according to claim 2, wherein said defect acquisition part handles each of a plurality of images included in said three or more captured images as said first captured image, handles each of a plurality of images included in said three or more captured images as said second captured image, and uses a plurality of combinations of said first captured image and said second captured image to acquire said defect candidate region.

4. The defect detection device according to claim 1, wherein said defect acquisition part acquires said defect candidate region in which said first dark region and said second light region overlap as a first defect candidate region, acquires, in said first captured image, a region whose lightness is higher than the lightness of the first reference image and higher than a value that satisfies a predetermined condition as a first light region, acquires, in said second captured image, a region whose lightness is lower than the lightness of the second reference image and lower than a value that satisfies a predetermined condition as a second dark region, acquires a region of overlap between said first light region and said second dark region as a second defect candidate region, acquires a region in which said first defect candidate region and said second defect candidate region are adjacent to each other as a third defect candidate region, and acquires an existence of a defect on the basis of said third defect candidate region.

5. The defect detection device according to claim 1, wherein said defect acquisition part expands said first dark region and said second light region and acquires a region of overlap between said first dark region and said second light region as a defect candidate region.

6. A defect detection device for detecting a surface defect in an object, comprising:

a light emission part capable of emitting light to an object from three or more directions that are different from one another;

an image capturing part for acquiring an image of a target region of a surface of said object;

an image capture controller for causing said image capturing part to acquire three or more captured images by acquiring an image while said object is being irradiated with light from each of said three or more directions; and a defect acquisition part for acquiring, in each captured image of a first predetermined number or more of captured images among said three or more captured images, a region whose lightness is lower than a lightness of a corresponding first reference image and lower than a value that satisfies a predetermined condition determined for said each captured image as a first dark region, acquiring, in each captured image of a second predetermined number or more of captured images among said three or more captured images, a region whose lightness is higher than a lightness of a corresponding second reference image and higher than a value that satisfies a predetermined condition determined for said each captured image as a second light region, acquiring a region of overlap between said first dark region and said second light region as a defect candidate region, and acquiring an existence of a defect on the basis of said defect candidate region.

7. The defect detection device according to claim 6, wherein said defect acquisition part expands said first dark region and said second light region and acquires a region of overlap between said first dark region and said second light region as a defect candidate region.

8. A defect detection method of detecting a surface defect in an object, comprising:

a) causing an image capturing part to acquire a first captured image of a target region of a surface of an object while said object is being irradiated with light from a first direction;

b) causing said image capturing part to acquire a second captured image of said target region while said object is being irradiated with light from a second direction different from said first direction;

c) acquiring, in said first captured image, a region whose lightness is lower than a lightness of a first reference image and lower than a value that satisfies a predetermined condition as a first dark region;

d) acquiring, in said second captured image, a region whose lightness is higher than a lightness of a second reference image and higher than a value that satisfies a predetermined condition as a second light region; and e) acquiring a region of overlap between said first dark region and said second light region as a defect candidate region and acquiring an existence of a defect on the basis of said defect candidate region.

9. The defect detection method according to claim 8, further comprising:

f) acquiring three or more captured images by causing said image capturing part to acquire an image of said target region while said object is being irradiated with light from each of three or more directions that are different from one another, wherein said step a) and said step b) are included in said step f), and one of said three or more captured images serves as said first captured image, and another of said three or more captured images serves as said second captured image.

10. The defect detection method according to claim 9, further comprising:
g) handling each of a plurality of images included in said three or more captured images as said first captured image, handling each of a plurality of images included in said three or more captured images as said second captured image, and performing said steps c) to e) on a plurality of combinations of said first captured image and said second captured image.

11. The defect detection method according to claim 8, wherein
in said step e), said defect candidate region in which said first dark region and said second light region overlap is acquired as a first defect candidate region,
the defect detection method further comprises:
f) acquiring, in said first captured image, a region whose lightness is higher than the lightness of the first reference image and higher than a value that satisfies a predetermined condition as a first light region;
g) acquiring, in said second captured image, a region whose lightness is lower than the lightness of the second reference image and lower than a value that satisfies a predetermined condition as a second dark region; and
h) acquiring a region of overlap between said first light region and said second dark region as a second defect candidate region, and
in said step e), a region in which said first defect candidate region and said second defect candidate region are adjacent to each other is acquired as a third defect candidate region, and an existence of a defect is acquired on the basis of said third defect candidate region.

12. The defect detection method according to claim 8, wherein
in said step e), said first dark region and said second light region are expanded and a region of overlap between said first dark region and said second light region is acquired as a defect candidate region.

13. A defect detection method of detecting a surface defect in an object, comprising:
a) acquiring three or more captured images by causing an image capturing part to acquire an image of a target region of a surface of an object while said object is being irradiated with light from each of three or more directions that are different from one another;
b) acquiring, in each captured image of a first predetermined number or more of captured images among said three or more captured images, a region whose lightness is lower than a lightness of a corresponding first reference image and lower than a value that satisfies a predetermined condition determined for said each captured image as a first dark region;
c) acquiring, in each captured image of a second predetermined number or more of captured images among said three or more captured images, a region whose lightness is higher than a lightness of a corresponding second reference image and higher than a value that satisfies a predetermined condition determined for said each captured image as a second light region; and
d) acquiring a region of overlap between said first dark region and said second light region as a defect candidate region and acquiring an existence of a defect on the basis of said defect candidate region.

14. The defect detection method according to claim 13, wherein
in said step d), said first dark region and said second light region are expanded and a region of overlap between said first dark region and said second light region is acquired as a defect candidate region.

* * * * *